United States Patent [19]

Towersey et al.

[11] Patent Number: 4,501,765
[45] Date of Patent: Feb. 26, 1985

[54] PRODUCTION OF EDIBLE PROTEIN-CONTAINING SUBSTANCES

[75] Inventors: Peter J. Towersey, High Wycombe; John Longton, Chesham; Geoffrey N. Cockram, Remenham Hill, all of England

[73] Assignee: Ranks Hovis McDougall Ltd., London, England

[21] Appl. No.: 411,805

[22] Filed: Aug. 26, 1982

Related U.S. Application Data

[63] Continuation of Ser. No. 813,188, Jul. 5, 1977, abandoned, which is a continuation of Ser. No. 584,451, Jun. 6, 1975, abandoned, which is a continuation of Ser. No. 440,775, Feb. 8, 1974, Pat. No. 3,937,693.

[30] Foreign Application Priority Data

Feb. 13, 1973 [GB] United Kingdom ................. 7087/73

[51] Int. Cl.$^3$ ............................................. A23J 3/00
[52] U.S. Cl. .................................... 426/656; 426/60; 260/112 R
[58] Field of Search .......................... 426/60, 62, 656; 260/112 R

[56] References Cited

U.S. PATENT DOCUMENTS 3,686,144  8/1972  Tamura et al. ................. 426/656 X
3,775,393 11/1973  Akin et al. ....................... 426/656 X
3,809,776  5/1974  Chao ................................ 426/656 X
3,865,951  2/1975  Spicer et al. ........................... 426/60
4,061,781 12/1977  Solomons et al. ..................... 426/60

Primary Examiner—Robert Yoncoskie
Attorney, Agent, or Firm—Stevens, Davis, Miller & Mosher

[57] ABSTRACT

Process for reducing the nucleic acid content in the production of an edible protein-containing substance comprising contacting a grown non-toxic microfungus of the class Fungi Imperfecti with a solvent comprising between 40% and 100% (by volume) of a lower alkanol containing up to three carbon atoms and thereafter incubating at a pH between 5 and 9.5 and at a temperature between 30° C. and 80° C. for a time of at least 90 seconds. There is disclosed an edible protein-containing substance of a non-viable edible non-toxic fungal mycelium of a non-toxic strain of the microfungus. The protein-containing substance is characterized by an essentially white color and improved ease of processing to a form suitable for food use.

17 Claims, No Drawings

PRODUCTION OF EDIBLE PROTEIN-CONTAINING SUBSTANCES

This is a continuation of application Ser. No. 813,188 filed July 5, 1977, now abandoned which in turn is a continuation of Ser. No. 584,451, filed June 6, 1975, now abandoned; which in turn is a Rule 60 continuation of Ser. No. 440,775, filed Feb. 8, 1974 (now U.S. Pat. No. 3,937,693).

This invention is for improvements in or relating to the production of edible protein containing substances.

It has particular reference to a process for reducing the nucleic acid content of microfungi.

British Pat. No. 1,210,356 describes and claims a process for the production of an edible protein-containing substance which comprises incubating and proliferating, under aerobic conditions, an organism which is a non-toxic strain of a microfungus of the class Fungi Imperfecti, in a culture medium containing essential growth-promoting nutrient substances, of which carbon in the form of assimilable carbohydrate constitutes the limiting substrate in proliferation, and separating from the assimilable carbohydrate exhausted medium the proliferated organism which constitutes the edible protein-containing substance.

British Pat. No. 1,331,471 describes and claims a process for the production of an edible protein-containing substance which comprises incubating and proliferating, under aerobic conditions, a non-toxic strain of *Penicillium notatum* or *Penicillium chrysogenum* or a variant or mutant thereof, in a culture medium containing essential growth-promoting nutrient substances, of which carbon in the form of assimilable carbohydrate constitutes the limiting substrate in proliferation, and separating from the assimilable carbohydrate exhausted medium the proliferated organism which constitutes the edible protein-containing substance.

British Pat. No. 1,331,472) describes and claims our specific novel strain of Penicillium notatum-chrysogenum IMI 138291 and variants and mutants thereof.

British Pat. No. 1,346,062) describes and claims a process for the production of an edible protein-containing substance which comprises incubating and proliferating, under aerobic conditions, a non-toxic strain of the genus Fusarium or a variant or mutant thereof, in a culture medium containing essential growth-promoting nutrient substances, of which carbon in the form of assimilable carbohydrate constitutes the limiting substrate in proliferation, and separating the proliferated organism comprising the edible protein-containing substance.

Our British specification No. 1,346,062 contains the following disclosure:

The present invention relates to a process for the production of edible protein-containing substances and has particular reference to the production of fungal protein by microbial action.

Our Specification No. 1,210,356 relates to a process for the production of an edible protein-containing substance which comprises incubating and proliferating, under aerobic conditions, an organism which is a non-toxic strain of a microfungus of the class Fungi Imperfecti, in a culture medium containing essential growth-promoting nutrient substances, of which carbon in the form of assimilable carbohydrate constitutes the limiting substrate in proliferation, and separating from an assimilable carbohydrate exhausted medium the proliferated organism which constitutes the edible protein-containing substance.

Our copending Application No. 8977/70, Ser. No. 1,331,471, claims an edible protein-containing substance comprising fungal mycelium possessing a high net protein utilization value on rat assays of at least 70 based on the α-amino nitrogen.

It is also an object of the present invention to provide an edible protein-containing substance comprising non-toxic fungal mycelium possessing a high net protein utilization value on rat assays of at least 65 preferably at least 70 based on the α-amino nitrogen and containing a non-toxic strain of the genus Fusarium or a variant or mutant thereof. The non-toxic mycelium possessing a high net protein utilization value of at least 70 based on the α-amino nitrogen may contain a non-toxic strain of the species *Fusarium graminearum*.

According to the present invention there is provided a process for the production of an edible protein-containing substance which comprises incubating and proliferating, under aerobic conditions, a non-toxic strain of the genus Fusarium or a variant or mutant thereof, in a culture medium containing essential growth-promoting nutrient substances, of which carbon in the form of assimilable carbohydrate constitutes the limiting substrate in proliferation, and separating the proliferated organism comprising the edible protein-containing substance.

The separated proliferated organism comprising the edible protein-containing substance may be incorporated into a foodstuff for human or animal consumption.

The substrate employed in the incubation stage may be of vegetable origin, for example starch, starch-containing materials or products of their hydrolysis, sucrose, sucrose-containing materials or hydrolysed sucrose i.e. invert sugar or mixtures thereof. Thus the substrate may comprise hydrolysed potato, molasses, glucose, maltose, hydrolysed bean starch or cassava. Alternatively substrate of animal origin comprising whey may be employed.

The non-toxic strain of Fusarium may be a strain of *Fusarium graminearum*.

The preferred non-toxic strain is our strain of *Fusarium graminearum* Schwabe, which is described and claimed together with variants and mutants thereof in copending United Kingdom Application No. 23452/70 (Ser. No. 1,346,061), has been deposited at the Commonwealth Mycological Institute, Kew, and assigned the number IMI 145425. It is non-pathogenic to wheat.

Our copending United Kingdom Application No. 23452/70 (Ser. No. 1,346,061) also describes and claims specifically five variants of our strain of *Fusarium graminearum* Schwabe IMI 145425 namely I-7, I-8, I-9, I-15 and I-16 deposited with the Commonwealth Mycological Institute and assigned the numbers IMI 154209, IMI 154211, IMI 154212, IMI 154213 and IMI 154210 respectively.

The temperature of incubation is in general between 25° and 34° C., preferably around 30° C.

Inoculation resulting in commencement of the process is carried out by a pregerminated seed stage comprising for example from 2% to 10% of inoculum, usually in the range 5% to 10% of inoculum based on final fermented operating volume.

The pH of the substrate medium during incubation is preferably kept within a suitable range supporting maximum growth, for example, between 3.5 to 7.

The period of growth in batch culture under the abovementioned conditions is usually found to range from 20 to 48 hours. In both batch and continuous processes aeration and agitation should be carried out to provide a sufficient level of dissolved oxygen to overcome deficiency which can be a limiting growth factor.

As will be well understood by those skilled in the art sufficient quantities of essential growth nutrients such as nitrogen, sulphur, phosphorus and other trace elements are maintained in the substrate medium so that growth of the substrate is limited only by the carbohydrate available to the fungus.

In addition to the nutrients stated above the presence of one or more vitamins such as for example biotin may be desirable to maintain maximum growth rate.

It is also desirable to add a non-toxic anti-foaming agent to the substrate medium to control foaming during the fermentation.

The substance produced according to the present invention may be isolated in any suitable manner known in the art. Thus the resulting mycelium may be recovered by separation, washing, filtration and drying. In this connection, however, it has been found that if the moisture content of the substance is reduced below a critical level of about 50% (w/w) by filtration under pressure the subsequent drying methods employed are not subjected to such stringent temperature limitations which is an important factor in the economic processing of these materials. The method of drying must not cause damage to the nutritional value of the mycelium and may be drying in a current of air at 75° C. or freeze drying.

The fungal mycelium produced by the process of the present invention shows very good water-binding capacity and may be useful as a thickening and gelling agent. Not being an isolate, it retains its vitamins as well as other nutritionally available materials such as lipids and some carbohydrates. Fungal mycelium has satisfactory baking characteristics which are of value in protein enriched breads, breakfast foods and food snacks. The fungal mycelium, because of its filamentous structure, can be baked, fried or puffed and presented to many communities as a food comparable in appearance and acceptability with conventional foods which they are accustomed to eating.

Following is a description by way of example of method of carrying the invention into effect.

Culture medium or medium percentages given are as weight per unit volume (w/v) or volume per unit volume (v/v) for solids and liquids respectively.

Definitions:
NPU=net protein utilization
NPUop=net protein utilization: operative $\mu:$ = a specific growth rate which is the rate of increase/unit of organism concentration $\left(\frac{i}{x} \frac{dx}{dt}\right)$.

$\mu$max. is the growth rate constant (the maximum value of $\mu$ at saturation levels of substrate).

Yield Factor: weight of organism formed/weight of substrate used.

Examples 1–4 are of batch culture.

EXAMPLE 1

10 Liters of the following culture medium were prepared and sterilized as described in a stirred fermenter vessel.

| | |
|---|---|
| Cane molasses to provide | 6% w/v sugar |
| Ammonium sulphate | 1.2% |
| NaH$_2$PO$_4$ | 0.25% |
| Sterilized 30 minutes | 15 psig |
| CaCO$_3$ | 0.5% w/v |
| Sterilized 3 hours | 15 psig |

The medium components were added aseptically and attemperated to 30° C. An inoculum equivalent to 5–10% by volume of the culture medium and grown either on a glucose/corn steep liquor medium or other suitable materials in shake flasks was inoculated with a spore suspension of the organism comprising our strain of *Fusarium graminearum* Schwabe IMI 145425, for 18–24 hours at 30° C. on a rotary shaker, and added aseptically to the fermenter.

The fermenter incubated at 30° C. was then stirred at 800 rpm with a 6 bladed disc turbine (C.5D) in a full baffled vessel and 1 VVM of sterile air passed through. After 35 hours, the grown mycelium was removed from the fermenter, centrifuged, washed with water and dried in a warm air band drier, air temperature 75° C.

The dried product had the following composition:

| | |
|---|---|
| Total Nitrogen | 8.0% |
| Ash | 5.3% |
| Liquid | 2.7% |
| NPUop. | 52 based on Total Nitrogen |

EXAMPLE 2

10 Liters of the following culture medium were prepared and sterilized as described, in a 14 liter New Brunswick, Microferm, fermenter.

| | | | Final % |
|---|---|---|---|
| Solution 1 | Glucose | pH 3.0 | 3.0 |
| Solution 2 | Ammonium sulphate | | 0.7 |
| Solution 3 | Potassium di-hydrogen phosphate | pH 5.0 | 1.0 |
| Solution 4 | FeSO$_4$ 7H$_2$O | pH 2.5 | 0.001 |
| | MnSO$_4$ 4H$_2$O | | 0.0005 |
| | CuSO$_4$ 5H$_2$O | | 0.0001 |
| | MgSO$_4$ 7H$_2$O | | 0.025 |
| Solution 5 | Na$_2$MoO$_4$ 2H$_2$O | | 0.0001 |
| | CoCl$_2$ 6H$_2$O | | 0.0015 |
| Solution 6 | NaOH | | 0.1 |

All the above solutions were sterilized by heat for 15 minutes at 15 psig.

Solution 7 Vitamins and/or amino acids as described below sterilized by filtration.

The solutions were added aseptically to the vessel.

An inoculum was grown and added as in Example 1 except tha the final concentration in the fermenter was adjusted so as to provide 0.5 gm/l dry wt. of mycelium.

The conditions of growth were temperature 30° C.; aeration 1 VVM, stirrer speed was adjusted to maintain a level of dissolved oxygen above 25% of the saturation value in the culture medium, measured by a New Brunswick Inc. DO probe. Sterile antifoam, polypropylene glycol 2000, was added as required to suppress foam and pH was maintained between 6.0–6.3 by the addition of sterile potassium hydroxide solution.

|     |     | Growth rates (hr.$^{-1}$) |
| --- | --- | --- |
| (i) | Omitting solution 7 (Minimal medium) | very slow |
| (ii) | Solution 7 such that the final concentration of Biotin in the culture medium was 50 μg/l | 0.2 |
| (iii) | Solution 7 such that the final concentration of Biotin in the culture medium was 50 μg/l; Choline chloride 30 mg/l and Methionine 300 mg/l | 0.25 |

EXAMPLE 3

Medium and conditions were as in Example 2, but the glucose was replaced with maltose.

| (i) | Solution 7 as Example 2 (ii) | 0.18 |
| --- | --- | --- |
| (ii) | Solution 7 as Example 2 (iii) | 0.21 |

EXAMPLE 4

100 Liters of the following culture medium were prepared and sterilized as described in a 130 l stainless steel fermenter.

|  | % Final concentration |
| --- | --- |
| Glucose | 4.0 |
| Corn steep liquor (50% Total Solids) | 0.8 |
| Ammonium sulphate | 0.2 |
| Potassium di-hydrogen phosphate | 0.2 |
| Mg SO$_4$ 7H$_2$O | 0.025 |
| Zn SO$_4$ 7H$_2$O | 0.0005 |
| Fe SO$_4$ 7H$_2$O | 0.0005 |
| Mn SO$_4$ 4H$_2$O | 0.0001 |

The medium was sterilized at pH 3.0 at 15 psig for 30 minutes and on cooling to 30° C. adjusted to pH 5.0 by the sterile addition of ammonia.

Biotin sterilized by filtration to give 40 μg/l final concentration, was added aseptically.

The vessel was inoculated with B 10 liters of culture grown in a sparged vessel, for 18 hours, at 30° C., on a medium containing: Glucose 2%; tryptone ("Oxoid") 0.4%; yeast extract ("Oxoid") 0.1%; ammonium sulphate 0.15%; potassium di-hydrogen phosphate 1%; sodium hydroxide 0.1%; magnesium sulphate 0.025%; ferrous sulphate 0.001%; zinc sulphate 0.001%; manganese sulphate 0.0005%; copper sulphate 0.001%; antifoam, polypropylene glycol 2000 0.05%, and sterilized for 45 minutes at 15 psig, inoculated with a spore suspension of our organism *Fusarium graminearum* Schwabe IMI 145425. The word "Oxoid" is a Registered Trade Mark.

The conditions for growth were temperature 30° C., aeration adjusted to provide dissolved oxygen concentrations above 10% of the saturation value for the culture broth. Sterile antifoam, polypropylene glycol 2000, was added to suppress foaming, and the pH was maintained at 5.0 by means of sterile ammonia additions. Samples of the mycelium were taken at intervals over the period of batch culture, filtered, washed with water and dried. On dry weight basis analysis gave Total nitrogen 8.0–8.6%; α-Amino nitrogen 6.4–6.6%. The initial growth rate in this complex medium derived from both the batched culture medium and inoculum was approximately 0.3 $hr.^{-1}$.

The following examples 5 and 6 are of continuous culture.

EXAMPLE 5

Culture medium of the following composition was prepared:

| | Final % |
|---|---|
| Solution 1 | |
| Glucose | 3.0 |
| Ammonium sulphate | 0.25 |
| Potassium di-hydrogen phosphate | 0.3 |
| Magnesium sulphate | 0.025 |
| Anti-foam, polypropylene glycol 2000 | 0.01 |
| Sterilized at pH 3.0 for 30 minutes at 15 psig | |
| Solution 2 | |
| $MnSO_4$ $4H_2O$ | 0.0005 |
| $FeSO_4$ $7H_2O$ | 0.0005 |
| $ZnSO_4$ $7H_2O$ | 0.0005 |
| $CoCl_2$ $6H_2O$ | 0.0001 |
| $CuSO_4$ $5H_2O$ | 0.0001 |
| $Na_2MoO_4$ $2H_2O$ | 0.0001 |
| Sterilized 15 minutes at 15 psig | |

Solution 3

Vitamins and/or amino acid as described below sterilized by filtration.

All solutions were added as necessary, aseptically. In 8.5 liter chemostat the conditions of growth were as follows:

Temperature 30° C.; aeration IVVM; agitation 800 rpm; single 6 bladed disc turbine 0.5 D in fully baffled vessel. Organism, our strain of *Fusarium graminearum* Schwabe IMI 145425. The pH maintained at 5.0 by automatic addition of sterile ammonia.

Samples were taken, filtered, washed with water and dried.

| | | μ Max. $hr.^{-1}$ | Yield factor | Mycelium TN % | Mycelium AN % | NPU based on TN | NPU based on AN |
|---|---|---|---|---|---|---|---|
| (i) | Solution 3 such that the final concentrate of Biotin in the culture medium was 20 μg/l | 0.17–0.19 | 0.5 | 7.2 to 7.9 | 6.3 to 6.8 | 54 | 65 |
| (ii) | Solution 3, such that the final concentration of Biotin in the culture medium was 20 μg/l and of methionine was 600 mg/l | 0.20–0.21 | 0.5 | 7.7 to 8.6 | 6.1 to 6.5 | 59 | 78 |

EXAMPLE 6

Culture medium of the following composition was prepared:

| | | |
|---|---|---|
| Bean starch (α-amylase treated) | 3.0 | carbohydrate |
| Corn steep liquor | 1.33 | |

-continued

| | |
|---|---|
| Ammonium sulphate | 0.25 |
| Potassium di-hydrogen phosphate | 0.15 |
| Magnesium sulphate | 0.025 |
| Antifoam polypropylene glycol 2000 (v/w) | 0.025 |
| Sterilized pH 4.0 for 30 minutes at 15 p.s.i.g. | |

The medium was fed to the 8.5 liter chemostat under the same conditions as in Example 5 except that the pH was varied between 3.5 and 6.0 and growth rate throughout 0.1 hr$^{-1}$. Samples were taken, filtered, washed with water and dried. The following result was obtained:

| | TN % | AN % | NPU based on TN | NPU based on AN |
|---|---|---|---|---|
| Product grown at pH 4.0 | 7.8 | 6.6 | 54 | 67 |
| Product grown at pH 5.0 | 8.6 | 7.1 | 57 | 71 |
| Product grown at pH 6.0 | 7.7 | 5.9 | 61 | 80 |

EXAMPLE 6(b)

The culture medium and conditions were as in Example 6 except that the pH was held at 5.0 throughout the run and the temperature was varied between 26° and 34° C. The optimum temperature was found to be 30°–32° C.

Examples 7 to 11 describe the fermentation of five variants or isolates of *Fusarium graminearum* Schwabe IMI 145425.

EXAMPLE 7

Duplicate shake flasks of 1-liter capacity were prepared containing 200 mls. of the following medium:

| | | Final concentration % |
|---|---|---|
| Solution 1 | Glucose (sterilized separately pH 3.0 10 p.s.i./10 min.) | 3.0 |
| Solution 2 | Ammonium sulphate | 0.565 |
| | Potassium Dihydrogen Phosphate | 1.0 |
| | $MgSO_4:7H_2O$ | 0.025 |
| | $FeSO_4:(NH_4)_2SO_4:6H_2O$ | 0.0005 |
| | $MnSO_4:4H_2O$ | 0.0005 |
| | $CuSO_4:5H_2O$ | 0.0001 |
| | $CoCl_2:6H_2O$ | 0.0001 |
| | $CaCl_2:2H_2O$ | 0.0015 |
| | $Na_2MoO_4\ 2H_2O$ | 0.00001 |
| | NaOH | 0.2 |

Salts sterilized at 15 p.s.i.g./15 min. Final pH 6.0
Solution 3 Vitamins as described below were sterilized by filtration.

The solutions were added aseptically to give a final volume of 200 ml. then the flasks were inoculated with washed spores of our strain of *Fusarium graminearum* I-7 IMI 154209 to give a concentration of $8\times10^3$/ml.

The conditions of growth were temperature 30° C., 140 r.p.m. on orbital shaker with 2" throw.

At hourly intervals the growth was measured by measuring the Optical Density of a sample at 600 mμ. From the results obtained the following growth rates were established.

| | | Growth rate $h^{-1}$ |
|---|---|---|
| (i) | Solution 3 omitted (minimum medium) | very slow |
| (ii) | Solution 3 such that the final concentration of Biotin in the culture medium was 50 μg/l | 0.22 |
| (iii) | Solution 3 such that the final concentration of Biotin in the culture medium was 50 g/l and Choline chloride 50 μmg/l. | 0.27 |

EXAMPLE 8

The procedure of Example 7 was repeated but the strain I-7 was replaced by our strain of *Fusarium graminearum* Schwabe I-8. The following growth rates were established:

| | | Growth rate $h^{-1}$ |
|---|---|---|
| (i) | As 7 (i) | very slow |
| (ii) | As 7 (ii) | 0.22 |
| (iii) | As 7 (iii) | 0.27 |

EXAMPLE 9

The procedure of Example 7 was repeated but the strain I-7 was replaced by our strain of *Fusarium graminearum* Schwabe I-9. The following growth rates were established:

| | | Growth rate $h^{-1}$ |
|---|---|---|
| (i) | As 7 (i) | very slow |
| (ii) | As 7 (ii) | 0.21 |
| (iii) | As 7 (iii) | 0.27 |

EXAMPLE 10

The procedure of Example 7 was repeated but the strain I-7 was replaced by our strain of *Fusarium graminearum* Schwabe I-15. The following growth rates were established:

| | | Growth rate $h^{-1}$ |
|---|---|---|
| (i) | As 7 (i) | very slow |
| (ii) | As 7 (ii) | 0.21 |
| (iii) | As 7 (iii) | 0.27 |

EXAMPLE 11

The procedure of Example 7 was repeated but the strain I-7 was replaced by our strain of *Fusarium graminearum* Schwabe I-16. The following growth rates were established:

| | | Growth rate$^{-1}$ |
|---|---|---|
| (i) | As 7 (i) | very slow |
| (ii) | As 7 (ii) | 0.21 |
| (iii) | As 7 (iii) | 0.27 |

EXAMPLE 12

The procedure of Example 7 was repeated but the strain I-7 was replaced by the parent strain *Fusarium graminearum* Schwabe IMI 145425. The following growth rates were established.

| | | Growth rate$^{-1}$ |
|---|---|---|
| (i) | As 7 (i) | very slow |
| (ii) | As 7 (ii) | 0.22 |
| (iii) | As 7 (iii) | 0.27 |

Examples 13 and 14 describe fermentation using strains of Fusaria other than *Fusarium gramineareum.*

EXAMPLE 13

A spore suspension of *Fusarium solani* strain A7-16 (IMI 154217) was inoculated into a seed fermenter of 80 liter volume containing a glucose, corn steep liquor medium. After growing up the seed fermenter to 10–20 gms per liter, it was split in two, 40 liters to each 400 liter vessel. The seed was inoculated into a medium of the following composition:

| | % |
|---|---|
| Starch | 6.0 |
| $KH_2PO_4$ | 0.20 |
| $(NH_4)_2SO_4$ | 0.25 |
| Corn Steep Liquor 50% Total Solids) | 0.50 | pH was 5.5 maintained by addition of sterile ammonia; Temperature 30° C. Pressure 30 p.s.i.g. Air rate 1.0 v.v.m. The revolutions of the stirrer were increased steadily from 92 to 184 r.p.m. to maintain dissolved oxygen in the vessel. The agitator consisted of two turbines 0.4D. When the carbohydrate had been utilized the grown mycelium was removed from the fermenter, filtered, washed with water, centrifuged, and dried in a warm air band drier at 75° C. The dried product had the following composition:

| | |
|---|---|
| Total nitrogen | 9.1% |
| Ash | 8.3% |

When fed to rats this material gave an NPUop of 41 based on Total Nitrogen.

EXAMPLE 14

*Fusarium oxysporum* strain A9-23 (IMI 154214) was grown exactly as in the previous example except the starch was replaced by cane molasses at a concentration that produced 6.0% sugars.

The dried product had the following composition:

| | | |
|---|---|---|
| Total nitrogen | 9.9% | |
| Ash | 10.8% | |
| NPUop | 47.0 | based on Total Nitrogen |

Methods of analysis for Total Nitrogen (TN) Automatic Kjeldahl digestor (Technicon). A. Ferrari, Ann. N.Y. Sci. 87, 792 (1960).

Amino nitrogen (AN) 2:4:6-Tri-nitro benzene sulphuric acid (modified). M. A. Pinnegar, Technicon Symposium 1965, p. 80.

British Pat. No. 1,346,061 describes and claims our specific novel strain of *Fusarium graminearum* Schwabe IMI 145425 and variants and mutants thereof. This strain has also been deposited with the American Type Culture Collection and assigned the number A.T.C.C. 20334.

The separated proliferated organism comprising the edible protein-containing substance obtained by the fermentation processes of our British Pat. Nos. 1,331,471 and 1,346,062 may be incorporated into a foodstuff for human or animal consumption.

The processes of our British Pat. Nos. 1,331,471 and 1,346,062 are capable of producing an edible protein-containing substance comprising fungal mycelium which possesses a high net protein utilisation value on rat assays of at least 70 based on the $\alpha$-amino nitrogen.

If single-cell protein is to be used as a primary protein source for human consumption the World Health Organization has advised that the nucleic acid content should be reduced to a level which would allow a maximum intake in the range of 2 grams of nucleic acid per day.

For a processing method to be acceptable, it must not only decrease the nucleic acid level to the required degree, but it also must be inexpensive and must not contaminate the food product with undesirable chemicals.

It is an object of the present invention to provide a process for the reduction of levels of nucleic acid in particular ribonucleic acid (RNA) in proliferated microorganisms combined with the minimum loss of protein to render them more acceptable as human food.

We have developed a process for treating cells of grown non-toxic microfungus of the class Fungi Imperfecti which can meet the above requirements of the World Health Organisation.

The invention provides fungal mycelium possessing a reduced level of RNA of below 4%.

Thus the invention provides fungal mycelium containing *Fusarium graminearum* Schwabe IMI 145425 possessing a reduced level of RNA of below 3% by weight, preferably below 2% by weight.

The invention also provides fungal mycelium containing *Penicillium notatum-chrysogenum* IMI 138291 possessing a reduced level of RNA of below 4%

According to the present invention there is provided a process for reducing the nucleic acid content in the production of an edible protein-containing substance comprising contacting a grown non-toxic microfungus of the class Fungi Imperfecti with a solvent comprising between 40% and 100% (by volume) of a lower alkanol containing up to three carbon atoms and thereafter incubating at a pH betweeen 5 and 9.5 and at a temperature between 30° C. and 80° C. for a time of at least 90 seconds.

The process may be applied to a grown non-toxic strain of Fusarium, *Penicillium notatum* or *Ponicillium chrysogenum, Penicillium funiculosum* or *Aspergillus niger.*

The strain of Fuscarium may be a strain of *Fusarium graminearum* Schwabe in particular IMI 145425, *Fusarium oxysporum* or *Fusarium nolani* as described and claimed in British Pat. Nos. 1,346,061 and 1,346,062.

The strain of *Penicilium notatum* or *Penicillium chrysogenus* may be a strain of *Penicillim notatum -chrysogenum,* for example IMI 138291, as described and claimed in British Pat. Nos. 1,331,471 and 1,331,742.

The lower alkanol containing up to three carbon atoms may be methyl alcohol, ethyl alcohol, propyl alcohol or isopropyl alcohol. Ethyl alcohol and isopropyl alcohol are solvents permitted by the Solvents in Food Regulations, 1967. The preferred solvent in the process of the present invention is isopropyl alcohol (IPA). Instead of pure isopropyl alcohol aqueous solutions containing between 40 or 50% by volume and up to 100% I.P.A. may be employed.

The incubation may conveniently be carried out at a temperature between 45° C. and 60° C. for a time of between 1.5 minutes and 40 minutes.

The incubation step may conveniently be carried out in the presence of a buffer solution for example $NH_4Cl/NH_4OH$ or $NH_4Cl/HCl$.

The post fermentation process of the present invention for reducing the nucleic acid content of microorganisms is essentially a two stage process.

Stage 1

The grown microbial protein or fungal mycelium obtained for example by the fermentation process described and claimed in British Pat. Nos. 1,331,471 and 1,346,062 may be harvested, filtered to remove growth medium and washed, if desired. It may then be suspended in the alkanol solvent for example 1 minute at 20° C. or contacted with an alkanol solvent water mixture. The majority or all of the alkanol solvent may be removed by such methods as vacuum filtration, filter pressing or centrifugation. The duration of contact with the alkanol solvent may be varied but is generally in the range between 15 seconds and 15 minutes. The temperature may vary between 0° C. and 60° C.

Stage 2

The cells may then be brought into intimate contact with aqueous buffer solutions in the pH range 5 to 9.5. Thus the solvent treated cells may then be resuspended and incubated in aqueous buffer solution at pH 8.6 and temperature 45° C. An example of a suitable buffer solution is 0.1M ammonium chloride solution with ammonium hydroxide added to adjust the pH to 8.6.

The resulting treated cells may then be harvested again for example by filtration and washing with water and thereafter formulated into foods or dried by various methods.

When the process is carried out in the pilot-plant the pH is adjusted to 5 after RNA removal. The purpose of this acidification is twofold (a) the material becomes "whiter" and (b) the texture change and this enables harvesting by vacuum filtration to be carried out easier.

The resulting solvent treated microbial protein or fungal mycelium may have a RNA content of 1–4% compared to 7 to 10% of the untreated proliferated organism.

The cells may be analysed to determine their chemical composition and to evaluate the efficiency of the nucleic acid reduction process.

Following is a description by way of example of methods of carrying the invention into effect.

References to "Biomass Loss" denote weight lost during processing.

Ribonucleic acid (RNA) content was determined by a modification of the method of Schmidt G. and Thannhauser, S. J., J. Biol.Chem., 1945, 161, 83.

Method of analysis for Total Nitrogen (TN) Automatic Kjeldahl digestor (Technicon). A. Ferrari, Ann. N.Y. Sci. 87, 792 (1960).

Amino nitrogen (AN) TNBS (modified). M. A. Pinnegar, Technicon Symponium 1965, p. 80.

EXAMPLE A

REDUCTION OF THE NUCLEIC ACID LEVELS IN VARIOUS MICRO-ORGANISMS

*Fusarium graminearum* IMI 145425 was cultivated by the following procedure:

| Medium in distilled water: | |
|---|---|
| $K_2HPO_4$ | 15.05 $gL^{-1}$ |
| $(NH_4)_2HPO_4$ | 6.64 $gL^{-1}$ |
| tri Sodium Citrate | 15.7 $gL^{-1}$ |
| Citric Acid | 5.48 $gL^{-1}$ |
| $K_2SO_4$ | 1.0 $gL^{-1}$ |
| Choline chloride | 50 $mgL^{-1}$ |
| Biotin | 50 $\mu gL^{-1}$ |
| Glucose | 30 $gL^{-1}$ |
| Minimal Salts | |
| $MgCl_2.6H_2O$ | 0.2 $gL^{-1}$ |
| $ZnSO_4$ | 0.003 $gL^{-1}$ |
| $MnCl_24H_2O$ | 0.005 $gL^{-1}$ |
| $FoCl_3.6H_2O$ | 0.01 $gL^{-1}$ |
| $CuCl_2.6H_2O$ | 0.001 $gL^{-1}$ |
| $NaMoO_4.2H_2O$ | 0.001 $gL^{-1}$ |
| $CoCl_2.6H_2O$ | 0.001 $gL^{-1}$ |
| $CaCl_2.2H_2O$ | 0.015 $gL^{-1}$ |

Sterilisation

All components with the exception of glucose are sterilized together, and the amounts of these materials required for 1 liter of modium are dissolved, made up to 850 ml. and distributed into 5 1 liter conical flasks, each containing 170 ml. A 30% w/v solution of glucose is prepared and sterilised in 20 ml. portions in universal bottles. Sterilisation is effected in an autoclave at 15 p.s.i. for 15 minutes.

Growth conditions

Before inoculation with 10 ml. of a growing culture, the contents of one bottle of sterile glucose solution is added to each flask. Culture of A3/5 then proceeds on an Orbital Shaker, with 2 inch throw, at 160 r.p.m. and a temperature of 30° C. The culture is harvested after 18 hours.

Cells were collected and washed on a Buchner filtration system and treated as follows:

(i) Suspended in 66% v/v isopropyl alcohol for 1 minute at 20° C.
(ii) Isopropyl alcohol was removed by filtration.
(iii) The treated cells were incubated in 0.1M $NH_4Cl/NH_4OH$ buffer at pH 8.6 and 45° C. for various times. The incubations were carried out at a slurry concentration of approximately 10 g/l with stirring.

Results

| Micro-fungi | Treatment | Time of Incubation Minutes | % RNA Content | % Amino Nitrogen | % Total Nitrogen |
|---|---|---|---|---|---|
| F. graminearium | None | None | 10.86 | 7.57 | 9.80 |
| | Nucleic acid Reduction | Zero | 9.86 | 8.23 | 10.93 |
| | Nucleic acid Reduction | 20 | 2.29 | 8.84 | 10.43 |
| | Nucleic acid Reduction | 40 | 1.88 | 8.68 | 9.91 |
| | Nucleic acid Reduction | 60 | 1.69 | 8.73 | 10.56 |

Conclusion

The level of nucleic acid was effectively reduced by the treatment described.

*Penicillium notatum chrysogenum*.IMI 138291 was cultivated by the following procedure:

Medium
2%: Soluble starch
0.2%: Spray dried corn steep liquor
0.2%: Mycological peptone
0.4%: (NH$_4$)$_2$SO$_4$
0.2%: KH$_2$PO$_4$
1%: Sucrose The medium is made up with hot tap water, and dispensed in 200 ml. aliquots into conical shake flasks.

0.1 ml. of liquid amylase was added to each shake flask and incubated at 70° C. for 15 minutes so that the starch was broken down and the viscosity reduced.

Sterilisation

The flasks were sterilised in an autoclave at 15 p.s.i. for 20 minutes.

Growth conditions

A sporo inoculum was added to each flask and the culture grown at 30° C. on an orbital shaker with a 2 inch throw at 160 r.p.m. After growth for 24 hours, 10 ml. of the growing culture was used as growing inoculum which was added to more flasks containing the starch medium. Cells produced after a further 24 hour growth were harvested, washed and used as follows:

(i) Suspended in 66% (v/v) isopropyl alcohol for one minute at 20° C.
(ii) Isopropyl alcohol was removed by filtration.
(iii) The treated cells were incubated in 0.1M NH$_4$Cl/NH$_4$OH buffer at pH 8.6and 40° C. for various times. The incubations were carrried out at a slurry concentration of approximately 10 gm/l with stirring.

Results

| Microfungi | Treatment | Time of Incubation Minutes | % RNA content | % Amino Nitrogen | % Total Nitrogen | % Biomass Loss |
|---|---|---|---|---|---|---|
| P. notatum-chrysogenum | None | None | 7.19 | 5.78 | 7.58 | 0 |
| P. notatum-chrysogenum | Nucleic Acid Reduction | 15 | 3.60 | 6.64 | 8.47 | 30 |
| P. notatum-chrysogenum | Nucleic Acid Reduction | 40 | 3.25 | 6.47 | 8.52 | 32 |
| P. notatum-chrysogenum | Nucleic Acid Reduction | 60 | 3.32 | 6.34 | 8.04 | 32 |

Conclusion

The level of nucleic acid was reduced by the treatment described. *Penicillium funiculosum* IMI 79195 was cultivated by the following procedure:

| Medium | |
|---|---|
| KH$_2$PO$_4$ | 15 g/l |
| NaOH | 1 g/l |
| Dextran | 1 g/l |
| Castor Oil | 10 g/l |
| Solution A+ | 5 ml/l |
| Solution B+ | 5 ml/l |
| Solution C+ | 5 ml/l |
| Yeast extract | 10 g/l |

Minimal salts

| A+ | | B+ | | C+ | |
|---|---|---|---|---|---|
| MgSO$_4$ | 50 g/l | CaCl$_2$ | 3 g/l | FeSO$_4$ | 1 g/l |
| ZnSO$_4$ | 1 g/l | | | | |
| MnSO$_4$ | 1 g/l | CaCl$_2$ | 0.2 g/l | | |
| CuSO$_4$ | 0.2 g/l | | | | |

All in distilled water.

Sterilisation

Adjust pH of medium to 5.5 before sterilisation. Autoclave all components together. (50 minutes 15 p.s.i.)

Growth conditions
(Batch culture)
Volume 10 L (Fermenter)
Temperature 28° C.
Stirrer 400 r.p.m.
Air flow 10 l/minutes
Harvest time 80 hours
Inoculum size 5% by volume (shake flask culture)

Cells were collected and washed on a Buchner filtration system and treated as follows:

(i) Suspended in80% isopropyl alcohol for 1 minute at 20° C.
(ii) Isopropyl alcohol was removed by filtration.
(iii) The treated cells were incubated in 0.1M NH$_4$Cl/NH$_4$OH buffer at pH 8.6 and 37° C. for 60 minutes. The incubation was carried out at a slurry concentration of approximately 10 g/l with stirring.

Results

| Microorganism | Treatment | % RNA content | % Amine N | % Total N |
|---|---|---|---|---|
| P. funiculosum | None | 4.23 | 3.74 | 5.81 |
| P. funiculosum | Nucleic Acid Reduction | 2.80 | 4.46 | 7.34 |

Conclusion

The level of nucleic acid was reduced by the treatment described.

*Aspergillus niger* NRRL 330 was cultivated by the following procedure:

The medium and sterilisation procedure were identical to that described for *P. notatum-chrynogenum*.

Growth conditions were also identical except that cells grown directly from spores were used instead of cells cultivated from growing inoculum.

Cells were collected and washed on a Buchner filtration system and treated as follows:

(i) Suspended in 66% (v/v) isopropyl alcohol for 1 minute at 20° C.
(ii) Isopropyl alcohol was removed by filtration.

(iii) The treated cells were incubated in 0.1M NH4Cl/NH4OH buffer at pH 8.6 and 40° C. for various times. The incubations were carried out at a slurry concentration of approximately 10 g/l with stirring.

Results

| Micro-fungi | Treatment | Time of Incubation Minutes | % RNA Content | % Amino Nitrogen | % Total Nitrogen | % Biomass loss |
|---|---|---|---|---|---|---|
| A. niger | None | None | 6.36 | 4.03 | 5.70 | none |
| " | Nucleic acid Reduction | zero | | | | |
| " | Nucleic acid Reduction | 15 | 1.88 | 4.40 | 6.30 | 27 |
| " | Nucleic acid Reduction | 30 | 1.86 | 4.35 | 5.77 | 28 |
| " | Nucleic acid Reduction | 60 | 1.82 | 4.25 | 5.62 | 32 |

Conclusion

The level of nucleic acid was effectively reduced by the treatment described.

EXAMPLE B

EFFECT OF THE % ISO-PROPYL ALCOHOL ON THE EFFICIENCY OF THE NUCLEIC ACID REDUCTION PROCESS

F. gramincarum IMI 145425, cultivated as described in Example A, was contacted with various isopropyl alcohol/water mixtures at 20° C. for 2 minutes. The treated cells were then incubated in 0.1M NH4Cl/NH4OH buffer pH 8.5 at 37° C. for 20 minutes. The incubations were carried out at a slurry concentration of approximately 10 g/l with stirring.

Results

| % IPA (by volume) | Treatment | % Biomass loss | % RNA remaining |
|---|---|---|---|
| 0 | None | 0.0 | 9.33 |
| 0 | Nucleic acid reduction | 1.8 | 9.33 |
| 10 | Nucleic acid reduction | 1.1 | 10.68 |
| 20 | Nucleic acid reduction | 11.3 | 9.74 |
| 30 | Nucleic acid reduction | 19.4 | 8.87 |
| 40 | Nucleic acid reduction | 25.6 | 4.58 |
| 50 | Nucleic acid reduction | 26.5 | 3.03 |
| 60 | Nucleic acid reduction | 28.0 | 3.25 |
| 70 | Nucleic acid reduction | 27.6 | 2.86 |
| 80 | Nucleic acid reduction | 26.3 | 3.35 |
| 90 | Nucleic acid reduction | 23.8 | 3.69 |
| 100 | Nucleic acid reduction | 25.1 | 4.58 |

Conclusion

The nucleic acid removal process is most effective in the range of 40–100% isopropyl alcohol.

In the case of the treatment with 10 & 20% IPA the final RNA content is greater than the starting material; this is because RNA is removed to a lesser extent than biomass lost.

EXAMPLE C

EFFECT OF CONTACT WITH IPA AT VARIOUS TEMPERATURES ON THE SUBSEQUENT NUCLEIC ACID REDUCTION PROCESS

F. graminearum IMI 145425, cultivated as described in Example A, was contacted with 100% IPA at 0°, 20°, 40°, and 60° C. for 2 minutes, then incubated with 0.1M NH4Cl/NH4OH buffer pH 8.5 for 20 minutes at 39° C. The incubations were carried out at a slurry concentration of approximately 10 g/l with stirring.

Results

| Temperature of IPA treatment | % RNA remaining |
|---|---|
| No treatment | 9.04 |
| 0° C. | 3.42 |
| 20° C. | 3.47 |
| 40° C. | 2.52 |
| 60° C. | 2.33 |

Conclusion

The nucleic acid reduction process if effective over the temperature range studied.

EXAMPLE D

EFFECTIVENESS OF VARIOUS ALCOHOLS ON THE NUCLEIC ACID REDUCTION PROCESS

F. graminearum IMI 145425, cultivated as described in Example A, was contacted with 100% iso-propyl alcohol, 70% iso-propyl alcohol, 70% propyl alcohol, 100% ethyl alcohol or 100% methyl alcohol at 20° C. for two minutes, then incubated with 0.1N NH4Cl/NH4OH buffer pH 8.5 at 37° C. or 40° C. for various time periods. The incubations were carried out at a slurry concentration of approximately 10 g/l with stirring.

Results

| Alcohol used | Time and temperature of second incubation | % RNA remaining |
|---|---|---|
| None | None | 9.16 |
| 100% iso-propyl alcohol | 30 mins. at 37° C. | 2.53 |
| 100% iso-propyl alcohol | 120 mins. at 37° C. | 0.70 |
| 70% iso-propyl alcohol | 20 mins. at 40° C. | 1.81 |
| 70% propyl alcohol | 20 mins. at 40° C. | 1.93 |
| 100% ethyl alcohol | 30 mins. at 37° C. | 2.17 |
| 100% ethyl alcohol | 120 mins. at 37° C. | 0.64 |

-continued

| Alcohol used | Time and temperature of second incubation | % RNA remaining |
|---|---|---|
| 100% methyl alcohol | 30 mins. at 37° C. | 5.50 |
| 100% methyl alcohol | 120 mins. at 37° C. | 1.17 |

Conclusion

The RNA reduction process is successfully activated by a lower alkanol containing up to three carbon atoms.

EXAMPLE E

DURATION OF CONTACT WITH ISO-PROPYL ALCOHOL

F. graminearum IMI 145425, cultivated as described in Example A, was contacted with 66% (v/v) IPA at 20° C. for various times thon incubated in 0.1N NH$_4$Cl/NH$_4$OH buffer pH 8.5 at 37° C. for 60 minutes. The incubations were carried out at a slurry concentration of approximately 10 g/l with stirring.

| Contact time with 66% IPA | % RNA remaining | % Biomass lost |
|---|---|---|
| 0 | 9.25 | 0 |
| 15 seconds | 1.12 | 36 |
| 1 minute | 1.14 | 38 |
| 2 minutes | 0.98 | 40 |
| 5 minutes | 1.23 | — |
| 15 minutes | 1.27 | 41 |

Conclusion

Over the contact times studied nucleic acid removal was efficient. In practice the contact time for best RNA reduction is around 2 minutes, at longer contact times the % biomass lost tends to rise to unacceptably high values.

EXAMPLE F

EFFICIENCY OF NUCLEIC ACID REDUCTION WITH BUFFERS OVER A pH RANGE OF 4–10

F. graminearum IMI 145425, cultivated as described in Example A, was contacted with 100% iso-propyl alcohol at 20° C. and incubated with the following series of buffers at 30° C. for 3 hours. The incubations were carried out at a slurry concentration of approximately 10 g/l with stirring.

| Buffer in second stage | % RNA Remaining |
|---|---|
| 0.1M NH$_4$Cl + HCl to bring to pH 4.0 | 11.49 |
| 0.1M NH$_4$Cl + HCl to bring to pH 4.5 | 9.07 |
| 0.1M NH$_4$Cl + HCl to bring to pH 5.0 | 5.85 |
| 0.1M NH$_4$Cl + HCl to bring to pH 5.5 | 3.52 |
| 0.1M NH$_4$Cl + NH$_4$OH to bring to pH 6.0 | 2.63 |
| 0.1M NH$_4$Cl + NH$_4$OH to bring to pH 6.5 | 1.60 |
| 0.1M NH$_4$Cl + NH$_4$OH to bring to pH 7.0 | 0.96 |
| 0.1M NH$_4$Cl + NH$_4$OH to bring to pH 7.5 | 0.97 |
| 0.1M NH$_4$Cl + NH$_4$OH to bring to pH 8.0 | 0.59 |
| 0.1M NH$_4$Cl + NH$_4$OH to bring to pH 8.5 | 0.91 |
| 0.1M NH$_4$Cl + NH$_4$OH to bring to pH 9.0 | 1.69 |
| 0.1M NH$_4$Cl + NH$_4$OH to bring to pH 9.5 | 3.84 |
| 0.1M NH$_4$Cl + NH$_4$OH to bring to pH 10.0 | 7.00 |

Conclusion

The nucleic acid removal is effective with this buffer system over the pH range 5–9.5.

EXAMPLE G

EFFICIENCY OF NUCLEIC ACID REDUCTION CARRIED OUT IN BUFFERS OF VARYING IONIC STRENGTHS

F. graminearum IMI 145425 cultivated as described in Example A, was contacted with 66% (v/v) IPA at 20° C. for 1 minute, and incubated in buffers or non-buffered solutions of varying ionic strengths at 45° C. The incubations were carried out at approximately 10 g/l with stirring.

| Buffer system | Treatment | Time of incubation at 45° C. (Minutes) | % RNA | % Amino Nitrogen | % Total Nitrogen |
|---|---|---|---|---|---|
| None | None | None | 10.89 | 7.57 | 9.80 |
| Distilled water | Nucleic acid reduced | 0 | 11.21 | 7.82 | 10.53 |
|  |  | 20 | 7.38 | 8.07 | 10.22 |
| pH 5.7 |  | 40 | 4.79 | 7.97 | 10.12 |
|  |  | 60 | 2.57 | 8.40 | 9.84 |
| Non-buffered ammonia solution sufficient to bring to pH 8.5 | " | 0 | 11.17 | 8.35 | 10.81 |
|  |  | 20 | 4.54 | 8.85 | 10.07 |
|  |  | 40 | 3.14 | 8.85 | 10.68 |
|  |  | 60 | 2.55 | 8.79 | 10.30 |
| 0.02 M NH$_4$Cl/NH$_4$OH buffer pH 8.5 | " | 0 | 9.96 | 8.46 | 10.89 |
|  |  | 20 | 3.21 | 8.62 | 10.38 |
|  |  | 40 | 2.39 | 8.73 | 10.36 |
|  |  | 60 | 1.82 | 8.90 | 10.12 |
| 0.1M NH$_4$Cl/NH$_4$OH buffer pH 8.5 | " | 0 | 9.86 | 8.23 | 10.98 |
|  |  | 20 | 2.29 | 8.84 | 10.45 |
|  |  | 40 | 1.88 | 8.68 | 9.91 |
|  |  | 60 | 1.69 | 8.73 | 10.56 |
| 0.5M NH$_4$Cl/NH$_4$OH buffer pH 8.5 | " | 0 | 10.02 | 8.21 | 10.58 |
|  |  | 20 | 5.85 | 8.35 | 10.13 |
|  |  | 40 | 5.63 | 8.42 | 10.01 |
|  |  | 60 | 5.58 | 8.54 | 10.12 |
| 1.0M NH$_4$Cl/NH$_4$OH buffer pH 8.5 | " | 0 | 10.19 | 7.56 | 10.89 |
|  |  | 20 | 10.45 | 7.72 | 10.48 |
|  |  | 40 | 9.96 | 7.99 | 10.81 |

-continued

| Buffer system | Treatment | Time of incubation at 45° C. (Minutes) | % RNA | % Amino Nitrogen | % Total Nitrogen |
|---|---|---|---|---|---|
| | | 60 | 9.89 | 8.15 | 10.58 |

Conclusion

Nucleic acid is most effectively reduced at lower ionic strengths. The optimum conditions for rapid reduction being 0.1N buffer.

EXAMPLE H

THE NUCLEIC ACID REDUCTION PROCESS STUDIED AT VARIOUS TEMPERATURES

F. graminearum IMI 145425, cultivated as described in Example A, was contacted with 66% (v/v) IPA at 20° C. for 2 minutes, and incubated in 0.1M $NH_4Cl/NH_4OH$ buffer pH 8.5 for various durations at various temperatures. The incubations were carried out at approximately 10 g/l with stirring.

| | Results | |
|---|---|---|
| Temperature of buffer | Time of incubation minutes | % RNA remaining |
| Control | — | 9.44 |
| 30° C. | 0 | 10.83 |
| 30° C. | 20 | 8.40 |
| 30° C. | 40 | 7.06 |
| 30° C. | 60 | 7.45 |
| 30° C. | 90 | 4.76 |
| 30° C. | 120 | 4.11 |
| 37° C. | 0 | 10.12 |
| 37° C. | 20 | 5.02 |
| 37° C. | 40 | 3.55 |
| 37° C. | 60 | — |
| 37° C. | 90 | 1.80 |
| 37° C. | 120 | 1.02 |
| 45° C. | 0 | 10.09 |
| 45° C. | 20 | 2.58 |
| 45° C. | 40 | 0.99 |
| 45° C. | 60 | 0.69 |
| 45° C. | 90 | 0.69 |
| 45° C. | 120 | 0.61 |
| 55° C. | 1.5 | 2.16 |
| 55° C. | 3.0 | 1.10 |
| 55° C. | 4.5 | 0.76 |
| 60° C. | 1.5 | 1.96 |
| 60° C. | 3.0 | 1.78 |
| 60° C. | 4.5 | 1.11 |
| 70° C. | 2.0 | 4.19 |
| 70° C. | 3.5 | 3.30 |
| 70° C. | 5.0 | 3.56 |
| 80° C. | 1.5 | 5.65 |
| 80° C. | 3.0 | 5.40 |
| 80° C. | 4.5 | 5.31 |

Conclusion

Nucleic acid reduction takes place over the temperature range 30° C.–80° C. The most efficient conditions are at a temperature of 60° C., where satisfactory reduction of RNA was achieved within 90 seconds.

We claim:

1. An edible protein-containing substance of reduced nucleic acid content of between 1.7 and 0.59% obtained by a process consisting essentially of contacting a grown nontoxic microfungus of the genus Fusarium with a solvent comprising between 40% and 100% by volume of a lower alkanol containing up to three carbon atoms and the remainder being water, substantially separating said solvent from said microfungus, incubating said microfungus at a pH between 5 and 9.5 and at a temperature between 30° C. and 80° C. for a time of at least 90 seconds and thereafter recovering said microfungus as said edible protein-containing substance which is harvested by vacuum filtration in the form of a washed moist product suitable for food use, said substance having a filamentous structure due to the presence of retained fungal cell wall material and being characterized by improved ease of processing to a form suitable for food use and an improved whiter color such as to make the protein-containing substance compatible with food use.

2. An edible protein-containing substance as claimed in claim 1 wherein the strain of Fusarium is a strain of *Fusarium graminearum* Schwabe, *Fusarium oxysporum* or *Fusarium solani*.

3. An edible protein-containing substance as claimed in claim 2, wherein the strain of *Fusarium graminearum* Schwabe is a strain of *Fusarium graminearum* Schwabe deposited with the Commonwealth Mycological Institute and assigned the number IMI 145425 (A.T.C.C. 20334).

4. An edible protein-containing substance comprising a non-viable edible non-toxic fungal mycelium of a non-toxic strain of *Fusarium graminearum* possessing a reduced level of RNA of below 4%, and being further characterized by improved ease of processing to a form suitable for food use and an essentially white color such as to make the protein-containing substance compatible with food use and a filamentous structure due to the presence of retained fungal cell wall material.

5. An edible protein-containing substance comprising a non-viable edible non-toxic fungal mycelium of a non-toxic strain of *Penicillium notatum-chrysogenum* IMI 138291 possessing a reduced level of RNA of below 4%, and being further characterized by improved ease of processing to a form suitable for food use and an essentially white color such as to make the protein-containing substance compatible with food use and a filamentous structure due to the presence of retained fungal cell wall material.

6. An edible protein-containing substance comprising a non-viable edible non-toxic fungal mycelium of a non-toxic strain of *Fusarium graminearum* possessing a reduced level of RNA of below 1.5%, and being further characterized by improved ease of processing to a form suitable for food use and an essentially white color such as to make the protein-containing substance compatible with food use and a filamentous structure due to the presence of retained fungal cell wall material.

7. An edible protein-containing substance comprising a non-viable edible non-toxic fungal mycelium of a non-toxic strain of *Fusarium graminearum* possessing a reduced level of RNA of below 1.27%, and being further characterized by improved ease of processing to a form suitable for food use and an essentially white color such as to make the protein-containing substance compatible with food use and a filamentous structure due to the presence of retained fungal cell wall material.

8. An edible protein-containing substance comprising a non-viable edible non-toxic fungal mycelium of a non-toxic strain of *Fusarium graminearum* possessing a reduced level of RNA of below 1%, and being further characterized by improved ease of processing to a form suitable for food use and an essentially white color such as to make the protein-containing substance compatible with food use and a filamentous structure due to the presence of retained fungal cell wall material.

9. An edible protein-containing substance comprising a non-viable edible non-toxic fungal mycelium of a non-toxic strain of *Fusarium graminearum* Schwabe IMI 145425 (A.T.C.C. No. 20334) possessing a reduced level of RNA of below 0.99%, and being further characterized by improved ease of processing to a form suitable for food use and an essentially white color such as to make the protein-containing substance compatible with food use and a filamentous structure due to the presence of retained fungal cell wall material.

10. An edible protein-containing substance comprising a non-viable edible non-toxic fungal mycelium of a non-toxic strain of *Fusarium graminearum* possessing a reduced level of RNA of below 0.70%, and being further characterized by improved ease of processing to a form suitable for food use and an essentially white color such as to make the protein-containing substance compatible with food use and a filamentous structure due to the presence of retained fungal cell wall material.

11. An edible protein-containing substance comprising a non-viable edible non-toxic fungal mycelium of a non-toxic strain of *Fusarium graminearum* possessing a reduced level of RNA of between about 1.27% and about 0.59%, and being further characterized by improved ease of processing to a form suitable for food use and an essentially white color such as to make the protein-containing substance compatible with food use and a filamentous structure due to the presence of retained fungal cell wall material.

12. An edible protein-containing substance comprising a non-viable edible non-toxic fungal mycelium of a non-toxic strain of *Fusarium graminearum* Schwabe IMI 145425 (A.T.C.C. No. 20334) possessing a reduced level of RNA of between about 0.99% and about 0.59%, and being further characterized by improved ease of processing to a form suitable for food use and an essentially white color such as to make the protein-containing substance compatible with food use and a filamentous structure due to the presence of retained fungal cell wall material.

13. An edible protein-containing substance comprising a non-viable edible non-toxic fungal mycelium of a non-toxic strain of *Fusarium graminearum* Schwabe IMI 145425 (A.T.C.C. No. 20334) possessing a reduced level of RNA of between about 1.70% and about 0.59%, and being further characterized by improved ease of processing to a form suitable for food use and an essentially white color such as to make the protein-containing substance compatible with food use and a filamentous structure due to the presence of retained fungal cell wall material.

14. An edible protein-containing substance in the form of a washed product suitable for food use comprising a non-viable edible non-toxic fungal mycelium of a non-toxic strain of *Fusarium graminearum*, said product having a filamentous structure due to the presence of retained fungal cell wall material and possessing a reduced level of RNA of below 3%, and being further characterized by improved ease of processing to a form suitable for food use and an essentially white color such as to make the protein-containing substance compatible with food use.

15. An edible protein-containing substance comprising a non-viable edible non-toxic fungal mycelium of a non-toxic strain of *Fusarium graminearum* Schwabe IMI 145425 (A.T.C.C. No. 20334), said product having a high net protein utilization value of the order of 67 or above based on $\alpha$-amino nitrogen and possessing a reduced level of RNA of below 1.5%, and being further characterized by an essentially white color such as to make the protein-containing substance compatible with food use and a filamentous structure due to the presence of retained fungal cell wall material and being capable of processing by vacuum filtration and washing on the filter in the form of a moist product suitable for food use.

16. An edible protein-containing substance comprising a non-viable edible non-toxic fungal mycelium of a non-toxic strain of *Fusarium graminearum*, said product having a high net protein utilization value of the order of 52 or above based on the total nitrogen and possessing a reduced level of RNA of below 1.5%, and being further characterized by improved ease of processing to a form suitable for food use and an essentially white color such as to make the protein-containing substance compatible with food use and a filamentous structure due to the presence of retained fungal cell wall material.

17. An edible protein-containing substance comprising a non-viable edible non-toxic fungal mycelium of a non-toxic strain of *Fusarium graminearum* Schwabe IMI 145425 (A.T.C.C. No. 20334), said product having a high net protein utilization value of the order of 67 or above based on $\alpha$-amino nitrogen and possessing a reduced level of RNA of below about 0.59%, and being further characterized by an improved whiter color such as to make the protein-containing substance compatible with food use and a filamentous structure due to the presence of retained fungal cell wall material and being capable of processing by vacuum filtration in the form of a washed moist product suitable for food use.

* * * * *

UNITED STATES PATENT AND TRADEMARK OFFICE
CERTIFICATE OF CORRECTION

PATENT NO. : 4,501,765

DATED : February 26, 1985

INVENTOR(S) : Peter J. TOWERSEY, et al.

It is certified that error appears in the above-identified patent and that said Letters Patent is hereby corrected as shown below:

Column 4, line 34, "Liquid" should be -- Lipid --;

line 61, "tha" should be -- that --.

Column 5, line 45, "B" should be deleted.

Column 6, line 66, "%" should be inserted above the numeral column.

Column 8, line 8, "g" should be --$\mu$g --;

line 9, "$\nu$mg" should be --$\mu$g--.

UNITED STATES PATENT AND TRADEMARK OFFICE
CERTIFICATE OF CORRECTION

PATENT NO. : 4,501,765

DATED : February 26, 1985

INVENTOR(S) : Peter J. TOWERSEY, et al.

It is certified that error appears in the above-identified patent and that said Letters Patent is hereby corrected as shown below:

Column 10, line 54, "Fuscarium" should be -- Fusarium --;

line 56, "nolani" should be -- solani --;

line 58, "Penicilium" (first occurance) should be -- Penicillium --;

line 59, "chyrsogenus" should be -- chrysogenum --;

line 59, "Penicillim" should be -- Penicillium --.

Column 11, line 41, "change" should be -- changes --.

Column 12, line 14, "FoCl$_3$" should be -- FeCl$_3$ --;

line 22, "modium" should be -- medium --;

UNITED STATES PATENT AND TRADEMARK OFFICE
CERTIFICATE OF CORRECTION

PATENT NO. : 4,501,765

DATED : February 26, 1985

INVENTOR(S) : Peter J. TOWERSEY, et al.

It is certified that error appears in the above-identified patent and that said Letters Patent is hereby corrected as shown below:

Column 12, line 31, "flank" should be -- flask --;

line 49, "Troutment" should be -- Treatment --;

line 52, "F. graminearium" should be -- F. graminearum --;

line 55, "10.43" should be -- 10.45 --.

Column 13, last line, "$CaCl_2$" should be -- $CoCl_2$ --.

Column 16, line 51, "N" should be -- M --.

Column 17, line 18, "thon" should be -- then --;

line 18, "N" should be -- M --.

Column 19, line 13, "N" should be -- M --.

Signed and Sealed this

Third Day of December 1985

[SEAL]

Attest:

DONALD J. QUIGG

Attesting Officer

Commissioner of Patents and Trademarks